(12) United States Patent
Winternheimer

(10) Patent No.: US 10,245,200 B2
(45) Date of Patent: Apr. 2, 2019

(54) TRACTION DEVICE

(71) Applicant: Country View Medical Center, Wheaton, IL (US)

(72) Inventor: Jeffrey Winternheimer, Wheaton, IL (US)

(73) Assignee: Stella's Practice Management LLC, Wheaton, IL (US)

( * ) Notice: Subject to any disclaimer, the term of this patent is extended or adjusted under 35 U.S.C. 154(b) by 0 days.

(21) Appl. No.: 14/731,197

(22) Filed: Jun. 4, 2015

(65) Prior Publication Data

US 2015/0265481 A1    Sep. 24, 2015

Related U.S. Application Data

(63) Continuation of application No. 14/566,255, filed on Dec. 10, 2014.
(Continued)

(51) Int. Cl.
*A61F 5/045* (2006.01)
*A61G 13/00* (2006.01)
(Continued)

(52) U.S. Cl.
CPC ............... *A61G 13/009* (2013.01); *A61F 5/04* (2013.01); *A61G 13/1225* (2013.01);
(Continued)

(58) Field of Classification Search
CPC ............... A61H 1/0218; A61H 1/0229; A61H 2001/0233; A61H 2201/165;
(Continued)

(56) References Cited

U.S. PATENT DOCUMENTS 219,439 A * 9/1879 Blend .................. A63B 22/001
482/69
1,072,959 A * 9/1913 Kincannon .............. A47C 3/28
24/697.1
(Continued)

FOREIGN PATENT DOCUMENTS

JP    2005241479 A    9/2005

OTHER PUBLICATIONS

Unweighting and whole body vibration equipment, https://web.archive.org/web/20120125011342/http://www.pneumex.com, Jan. 25, 2012 (last visited Oct. 7, 2015).
(Continued)

*Primary Examiner* — Kari K Rodriquez
*Assistant Examiner* — Camtu T Nguyen
(74) *Attorney, Agent, or Firm* — McDonnell Boehnen Hulbert & Berghoff LLP

(57) ABSTRACT

Example traction devices, systems and methods for use thereof are provided. An example traction device may include (a) a frame comprising a top support having first and second ends, where the first end of the top support is coupled to a first vertical support and the second end of the top support is coupled to a second vertical support and (b) a balance bar moveably coupled to the top support via a wire, where opposing ends of the balance bar are each coupled to an attachment ring or define a receptacle.

14 Claims, 8 Drawing Sheets

Related U.S. Application Data

(60) Provisional application No. 61/914,006, filed on Dec. 10, 2013.

(51) Int. Cl.

| | | |
|---|---|---|
| *A61H 23/00* | (2006.01) | |
| *A61F 5/04* | (2006.01) | |
| *A61G 13/12* | (2006.01) | |
| *A61H 1/02* | (2006.01) | |
| *A61G 7/10* | (2006.01) | |
| *A63B 17/00* | (2006.01) | |
| *A63B 23/12* | (2006.01) | |
| *A63B 21/00* | (2006.01) | |

(52) U.S. Cl.
CPC ....... *A61G 13/1295* (2013.01); *A61H 1/0229* (2013.01); *A61H 1/0292* (2013.01); *A61H 23/00* (2013.01); *A61G 7/1015* (2013.01); *A61G 7/1044* (2013.01); *A61G 7/1051* (2013.01); *A61G 7/1061* (2013.01); *A61G 7/1078* (2013.01); *A61H 2201/0192* (2013.01); *A61H 2201/1619* (2013.01); *A61H 2201/1652* (2013.01); *A61H 2203/0487* (2013.01); *A63B 17/00* (2013.01); *A63B 21/00047* (2013.01); *A63B 23/1218* (2013.01)

(58) Field of Classification Search
CPC .... A61H 2201/1619; A61H 2201/1621; A61H 2201/1623; A61H 2201/1626; A61H 2201/1628; A61H 2201/163; A61H 2203/04; A61H 2203/0406; A61H 2203/0425; A61H 2206/0431; A61F 5/04; A61F 5/042; A61F 5/048
USPC .................................. 602/32, 34–36, 38–40
See application file for complete search history.

(56) References Cited

U.S. PATENT DOCUMENTS

| | | | | |
|---|---|---|---|---|
| 1,611,807 | A * | 12/1926 | Bergh | A61H 3/04 297/6 |
| 2,665,685 | A * | 1/1954 | Kaufman | A61H 1/0229 602/32 |
| 2,812,010 | A * | 11/1957 | Abdallah | A61H 3/008 482/69 |
| 2,830,581 | A * | 4/1958 | Sanders | A61H 1/0218 602/32 |
| 3,003,498 | A * | 10/1961 | Hotas | A61H 1/0218 602/32 |
| 3,238,936 | A * | 3/1966 | Siedentop | A61F 7/007 5/284 |
| 3,761,082 | A | 9/1973 | Barthel, Jr. | |
| 3,937,461 | A * | 2/1976 | Lew | A63B 7/02 182/6 |
| 4,431,184 | A * | 2/1984 | Lew | A63B 7/00 482/102 |
| 4,492,373 | A * | 1/1985 | Dzitzer | A63B 7/00 482/143 |
| 4,895,328 | A * | 1/1990 | Ryan | A61H 1/0229 248/124.1 |
| 4,898,378 | A | 2/1990 | Edwards et al. | |
| 5,000,440 | A * | 3/1991 | Lynch | A63B 21/0615 482/112 |
| 5,033,460 | A * | 7/1991 | Goldish | A61H 1/0218 606/241 |
| 5,181,904 | A | 1/1993 | Cook et al. | |
| 5,192,305 | A * | 3/1993 | Sastre | A61H 1/0229 606/241 |
| 5,273,502 | A * | 12/1993 | Kelsey | A61H 1/0229 482/66 |
| 5,333,333 | A * | 8/1994 | Mah | A61G 5/10 280/250.1 |
| 5,372,561 | A * | 12/1994 | Lynch | A63B 69/0064 482/54 |
| 5,403,270 | A * | 4/1995 | Schipper | A61H 1/0229 602/36 |
| 5,667,461 | A | 9/1997 | Hall | |
| 5,729,843 | A * | 3/1998 | Manthey | A61G 7/1017 5/89.1 |
| 6,273,844 | B1 | 8/2001 | Kelsey et al. | |
| 6,413,198 | B1 | 7/2002 | Gray | |
| 6,461,284 | B1 | 10/2002 | Francavilla | |
| 6,478,721 | B1 | 11/2002 | Hunter | |
| 6,554,747 | B1 | 4/2003 | Rempe | |
| 6,689,075 | B2 | 2/2004 | West | |
| 7,494,450 | B2 * | 2/2009 | Solomon | A61H 1/0229 482/51 |
| 7,794,372 | B1 | 9/2010 | Webber et al. | |
| 8,012,067 | B2 * | 9/2011 | Joannou | A61H 1/005 482/54 |
| 8,257,285 | B2 * | 9/2012 | Cook | A61H 1/005 5/915 |
| 2010/0331144 | A1 | 12/2010 | Rindfleisch | |
| 2013/0178767 | A1 | 7/2013 | Dreske | |

OTHER PUBLICATIONS

JP 2005241479 A—English Translation; Oho, Hisahito.

* cited by examiner

TRACTION DEVICE

CROSS-REFERENCE TO RELATED APPLICATION

This application claims the benefit of the filing date of U.S. Non-Provisional application Ser. No. 14/566,255, filed Dec. 10, 2014, which in turn claims priority to Provisional Application No. 61/914,006, filed Dec. 10, 2013, which are hereby incorporated by reference in their entirety.

BACKGROUND

Unless otherwise indicated herein, the materials described in this section are not prior art to the claims in this application and are not admitted to be prior art by inclusion in this section.

Traction beds are used for performing therapy on individuals having a myriad of injuries, pain, or other ailments. For example, traction beds are typically used for performing therapy on individuals having back pain to alleviate or reduce their back pain. Such therapy may involve stretching the individual's back by placing the individual into a harness, then strapping the harness at four different locations (i.e., upper left/right and lower left/right locations) to respective lever arms on the traction bed, and actuating the lever arms to pull on the harness. Known traction beds may be limited in capability to stretch the individual's back, may be painful for a patient to move into position on the table and may be painful or uncomfortable in use.

SUMMARY

Example embodiments beneficially provide traction devices and systems, as well as methods for use thereof that may permit upright nomadic decompression that may have decreased levels of discomfort for a patient over known traction devices and techniques. The amount of traction, flection and/or distraction may be advantageously controlled. For example, extenuation and/or diminishment of the lumbar curvature of a patient through gravitational pull may be achieved, while a patient is in suspension. Traction may be achieved using a balance bar and a tension wire of the invention with a patient in upright standing traction, in a seated position on a seat member with feet raised off the ground or free hanging from the suspension with feet up and back.

In an alternative arrangement, a patient may be suspended directly from the frame of the traction device and traction is induced through the action of gravity. This may result in a deep-seated stretch with the body fully relaxed. This arrangement may have the unique benefit of being able to provide both flection and distraction of the spine.

Thus, in one aspect, a traction device is provided including the features of (i) a frame comprising a top support having first and second ends, where the first end of the top support is coupled to a first vertical support and the second end of the top support is coupled to a second vertical support and (ii) a balance bar moveably coupled to the top support via a wire, where opposing ends of the balance bar are each coupled to an attachment ring or define a receptacle.

In a second aspect, a traction system is provided including the features of (i) a traction device that has (a) a frame comprising a top support having first and second ends, wherein the first end of the top support is coupled to a first vertical support and the second end of the top support is coupled to a second vertical support, (b) a balance bar moveably coupled to the top support via a wire, wherein opposing ends of the balance bar are each coupled to an attachment ring or define a receptacle, (c) at least two attachment rings either coupled to the top support or at least two receptacles defined by the top support, wherein the at least two attachment rings or receptacles are disposed between the first and the second vertical supports on opposite sides of the wire and (ii) a suspension harness that has (a) a torso-engaging portion, (b) a first strap and a second strap each attached at one end to a front of the torso-engaging portion and at another end to a back of the torso-engaging portion and (c) a lower-appendage support strap and (iii) where the first and second straps of the suspension harness are removably coupled to a first and a second attachment ring or receptacle of either the top support or the balance bar.

A third aspect provides a method to induce traction including the steps of (i) providing a traction device comprising (a) a frame comprising a top support having first and second ends, wherein the first end of the top support is moveably coupled to a first vertical support and the second end of the top support is coupled to a second vertical support, (b) a balance bar coupled to the top support via a wire, wherein opposing ends of the balance bar are each coupled to an attachment ring or define a receptacle, (c) at least two attachment rings either coupled to the top support or at least two receptacles defined by the top support, wherein the at least two attachment rings or receptacles are disposed between the first and the second vertical supports on opposite sides of the wire, (ii) providing a suspension harness comprising (a) a torso-engaging portion, (b) a first strap and a second strap each attached at one end to a front of the torso-engaging portion and at another end to a back of the torso-engaging portion and (c) a lower-appendage support strap, (iii) removably coupling the first and second straps of the suspension harness to a first and a second attachment ring or receptacle of the balance bar, via first and second linkages and (iv) placing the wire under tension via a pressure control system and raising the suspension harness.

These as well as other aspects, advantages, and alternatives, will become apparent to those of ordinary skill in the art by reading the following detailed description, with reference where appropriate to the accompanying drawings.

DETAILED DESCRIPTION

Figure 1:
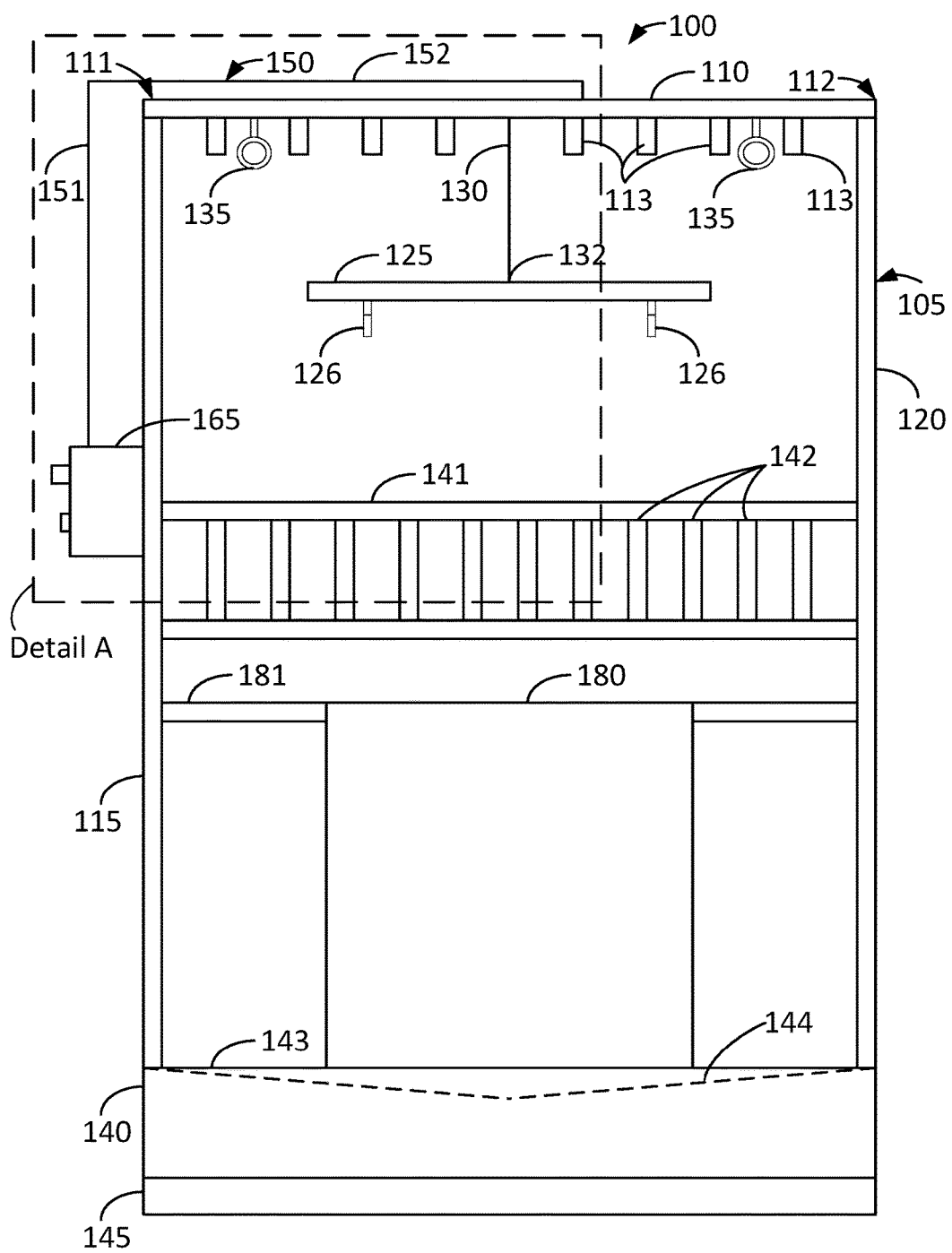
FIG. 1 is a front view of a traction device according to one example embodiment.

Example traction devices and systems, as well as methods of use thereof, are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

Referring to FIGS. 1-4, a traction device 100 is shown including a frame 105 having a top support 110 having first 111 and second ends 112. The first end 111 of the top support 110 is coupled to a first vertical support 115 and the second end 112 of the top support 110 is coupled to a second vertical support 120.

In addition, the traction device 100 includes a balance bar 125 is moveably coupled to the top support 110 via a wire 130. Opposing ends of the balance bar 125 are each coupled to an attachment ring 126 or define a receptacle 127. In one embodiment, a plurality of attachment rings 126 may be coupled to the balance bar or a plurality of receptacles 127 may be defined by the balance bar 125 (shown in dashed lines in FIG. 1A). These attachment rings 126 or receptacles 127 are arranged along a length of the balance bar 125 and may permit patient-specific adjustments to be made during treatment. The attachment rings and receptacles are not limited to a ring-shaped configuration per se, and may include any polygonal, circular or hook shaped configuration capable of receiving corresponding linkage from a strap on a harness, for example, such as a hook, carabineer, O-ring or D-ring.

In one embodiment, the top support 110 may be coupled to at least two attachment rings 135 or may define least two receptacles 136. These attachment rings or receptacles may be disposed between the first and the second vertical supports 115, 120 on opposite sides of the wire 130. In a further embodiment, a first plurality of attachment rings 135 may be coupled to the top support 110 or a first plurality of receptacles 136 may be defined in the top support 110 (shown in dashed lines in FIG. 1A). These first attachment rings or receptacles may extend between the first vertical support 111 and the wire 130. Likewise, a plurality of second attachment rings 135 may be coupled to the top support 110 or a second plurality of receptacles 136 may be defined in the top support 110 (shown in dashed lines in FIG. 1A). These second attachment rings 135 or receptacles 136 may extend between the second vertical support 112 and the wire 130. The attachment rings and receptacles discussed above with respect to the balance bar 125 are equally applicable to those of the top support 110.

In another embodiment, the traction device 100 may further include a base 140 that may be coupled to an end of the first vertical support 115 and to an end of the second vertical support 120 that are arranged opposite to the top support 110. The base 140 may have a planar top surface 143 or concave top surface 144, as shown in FIG. 1. If a seat member is part of the traction device, the concave top surface may help the seat member stay properly aligned with the frame 105.

In still a further embodiment, the traction device 100 may also include a vibration apparatus 145 coupled to one or more of the base 140 and the frame 105. In operation, the vibration apparatus may advantageously increase a patient's blood flow.

In one embodiment, traction device 100 may further include a housing 150 that may be coupled to the top support 110. The housing 150 may define a conduit 155 to receive and house the wire 130. In one embodiment, the housing 150 may include a vertical section 151 and a horizontal section 152. The vertical section 151 may be disposed adjacent either the first or the second vertical support 115, 120 and the horizontal section 152 may be disposed adjacent to the top support 110 of the frame 105. A piston 160 may be arranged within a cylinder 161 and may be disposed in the conduit 155. And a pressure control system 165 may be configured to move the piston 160 within the cylinder 161. The wire 130 has a first end 131 and a second end 132 arranged such that the first end 131 is coupled to the piston 160 and the second end 132 is coupled to the center of the balance bar 125.

In one embodiment, a first rotatable support 170 may be disposed in the housing 150 adjacent to a location at which the wire 130 extends from the housing 150 or the top support 110. The first rotatable support 170 is in mechanical communication with the wire 130. In another embodiment, a second rotatable support 175 may be disposed in the housing 150 between the piston 160 and the first rotatable support 170 at a junction of the vertical section 151 and the horizontal section 152 of the housing 150. The second rotatable support 175 is in mechanical communication with the wire 130. The rotatable supports 170, 175 may include a pulley, a roller, a bearing or any other mechanism capable of interfacing with a wire in motion to reduce friction and help advance the wire.

In one embodiment, the traction device 100 may further include a foot platform 180 coupled to one or more of the frame 105 or the base 140 via rigid bars 181, for example. The foot platform 180 is preferably angled outwardly from the frame 105 and base 140. In another embodiment, hand rails 141 may extend between the first vertical support 115 and the second vertical support 120 above the foot platform 180. These hand rails 141 may have a plurality of grips 142 extending there between. The rails 141 and grips 142 are positioned in a patient-facing manner to facilitate with traction-related exercises, for example. Similarly, the first and second vertical supports 115, 120 may each include a plurality of hand rails or grips 116, 121 having a vertically-extending, spaced-apart arrangement. And the top support 110 may also include a plurality of hand rails or grips 113 having a spaced-apart arrangement. All of the foregoing hand rails and grips may be utilized to execute stretches and traction exercises, for example.

The traction device 100 may also include a seat member 185 movably coupled to the frame 105 or in mechanical communication with a top surface 143 of the base 140. The seat member 185 may take the form of a gym or balance ball, in one embodiment. In one embodiment, a seat member 185 taking the form of a gym or balance ball, for example may be disposed beneath the patient. In alternative embodiments, the seat member may include a platform configured to interface with a patient's buttocks and may be movably coupled to the frame 105.

Figure 1A:
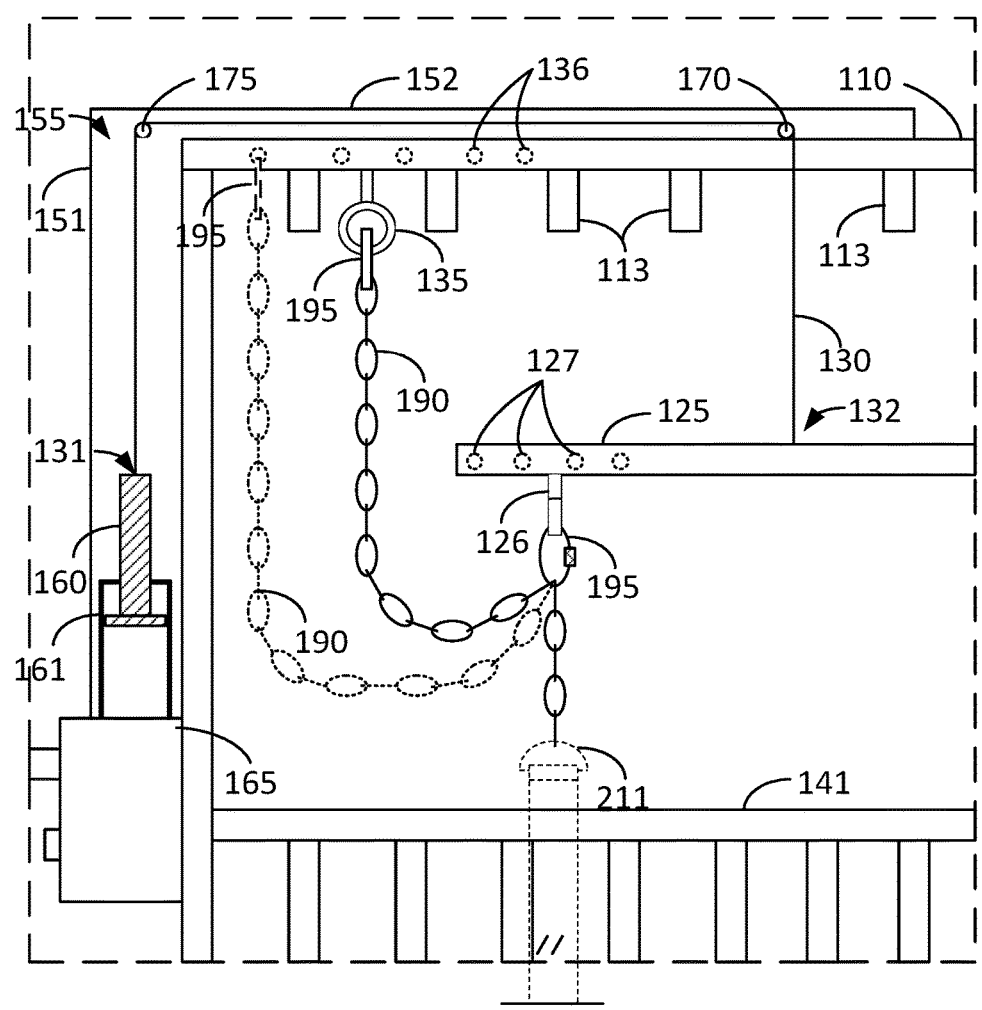
FIG. 1A is a detail view of FIG. 1 showing a cross-sectional front view of the housing according to one example embodiment and a front view of two suspension mechanisms according to one example embodiment.
Figure 2:
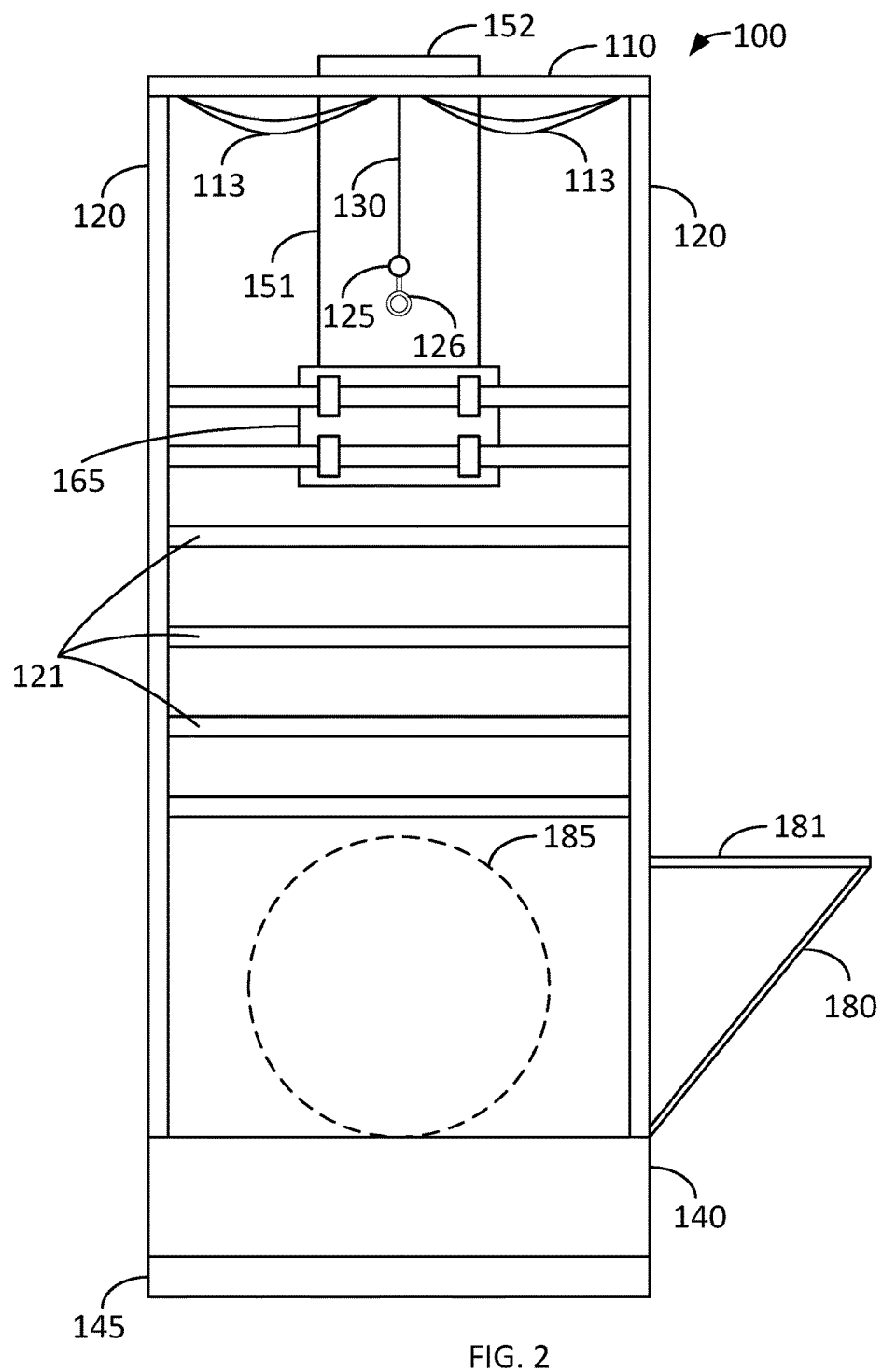
FIG. 2 is a right side view of the traction device of the example embodiment shown in FIG. 1.
Figure 3:
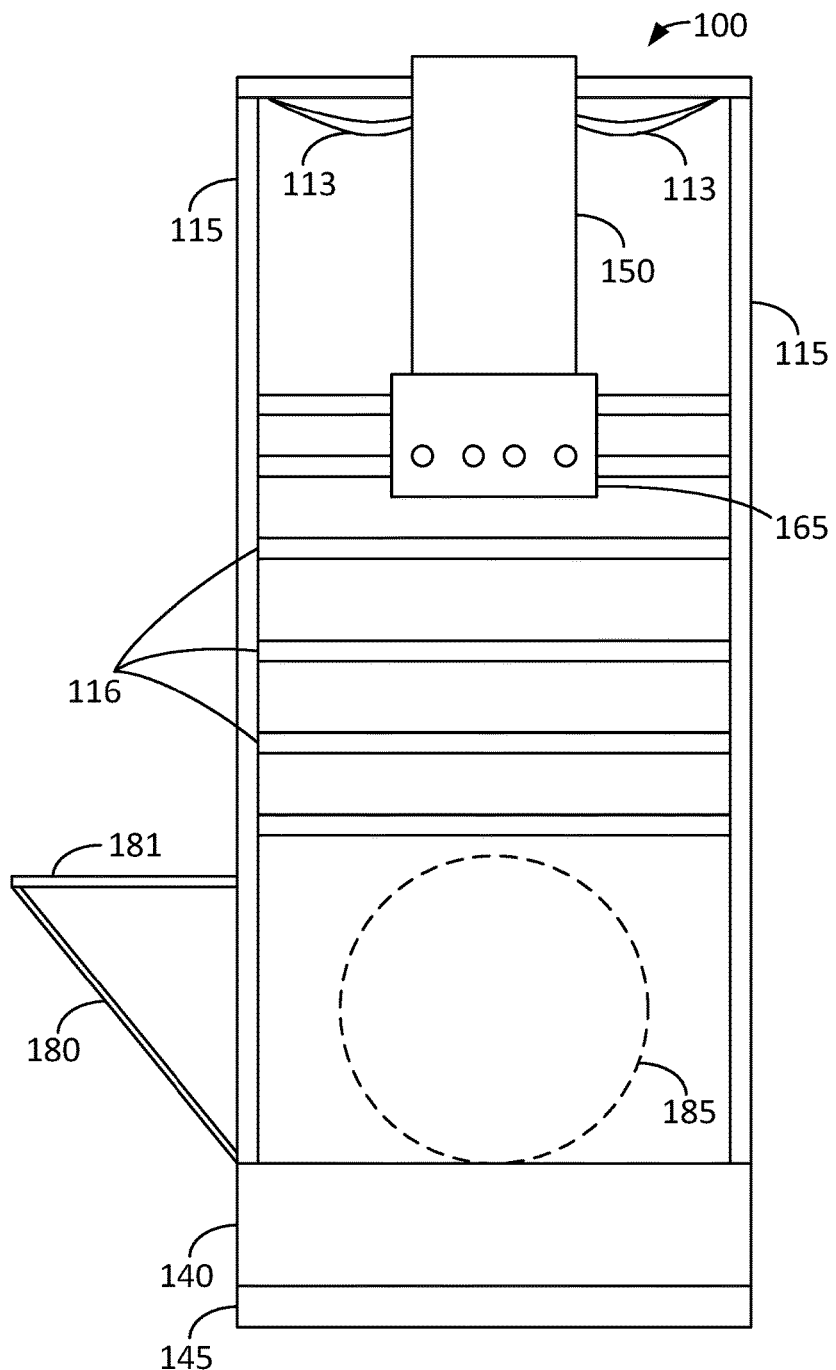
FIG. 3 is a left side view of the traction device of the example embodiment shown in FIG. 1.
Figure 4:
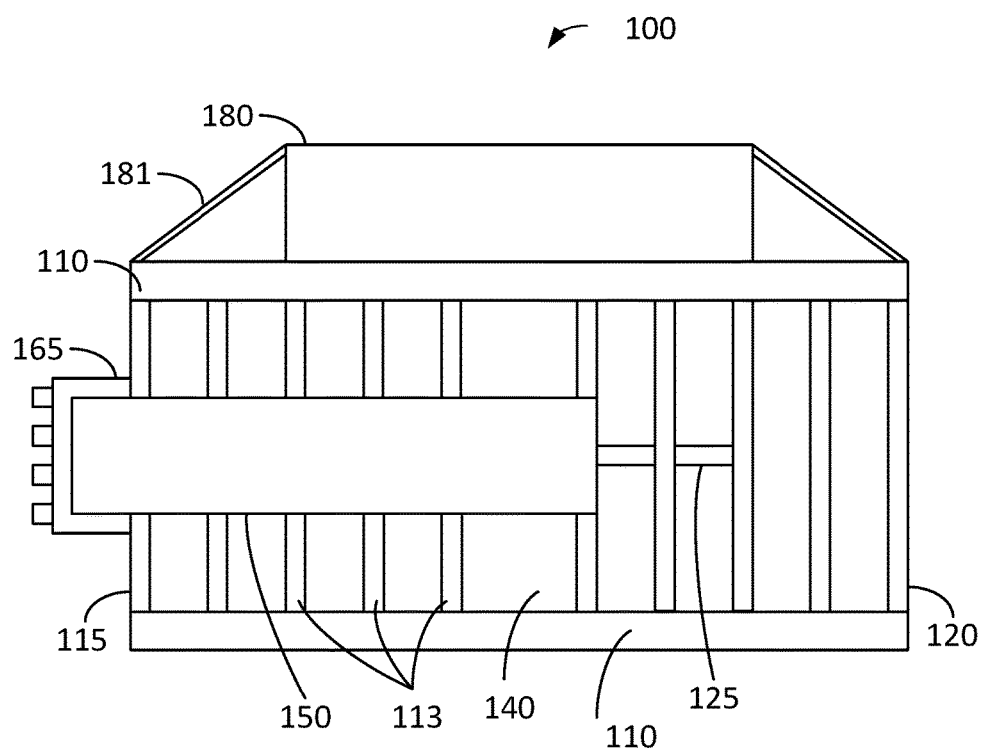
FIG. 4 is a top view of the traction device of the example embodiment shown in FIG. 1.
Figure 5:
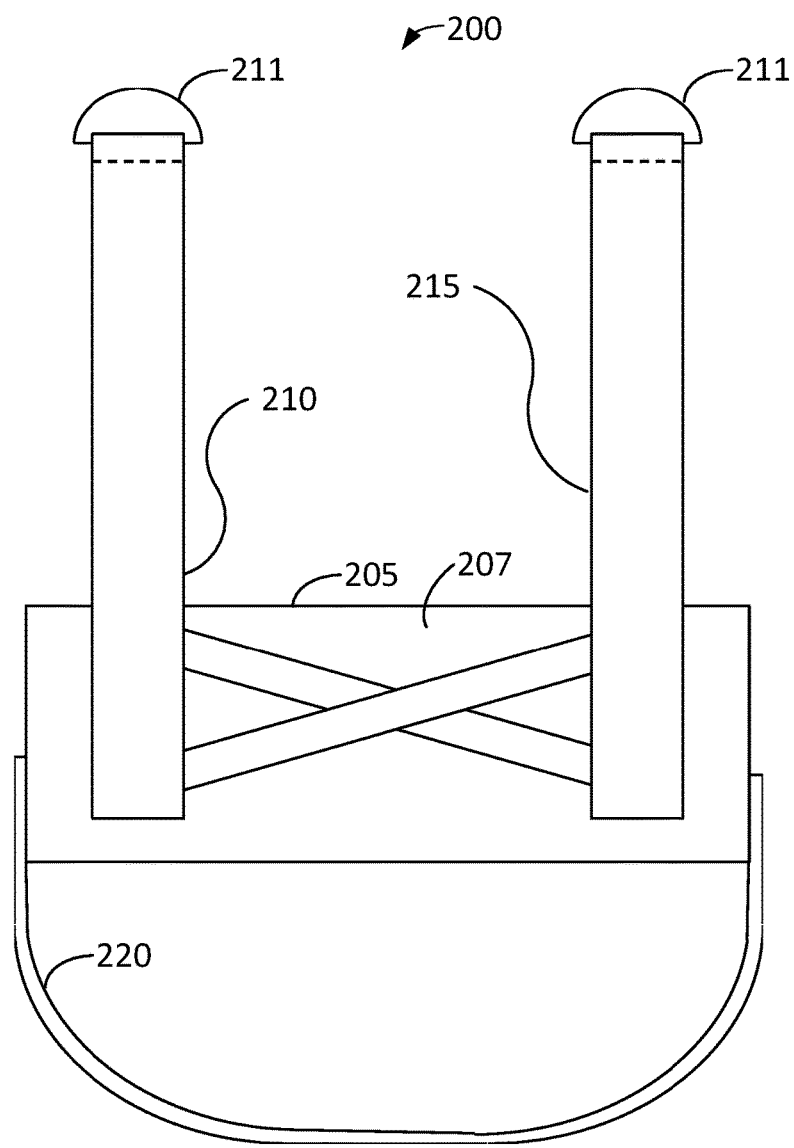
FIG. 5 is a back view of a suspension harness according to one example embodiment.
Figure 6:
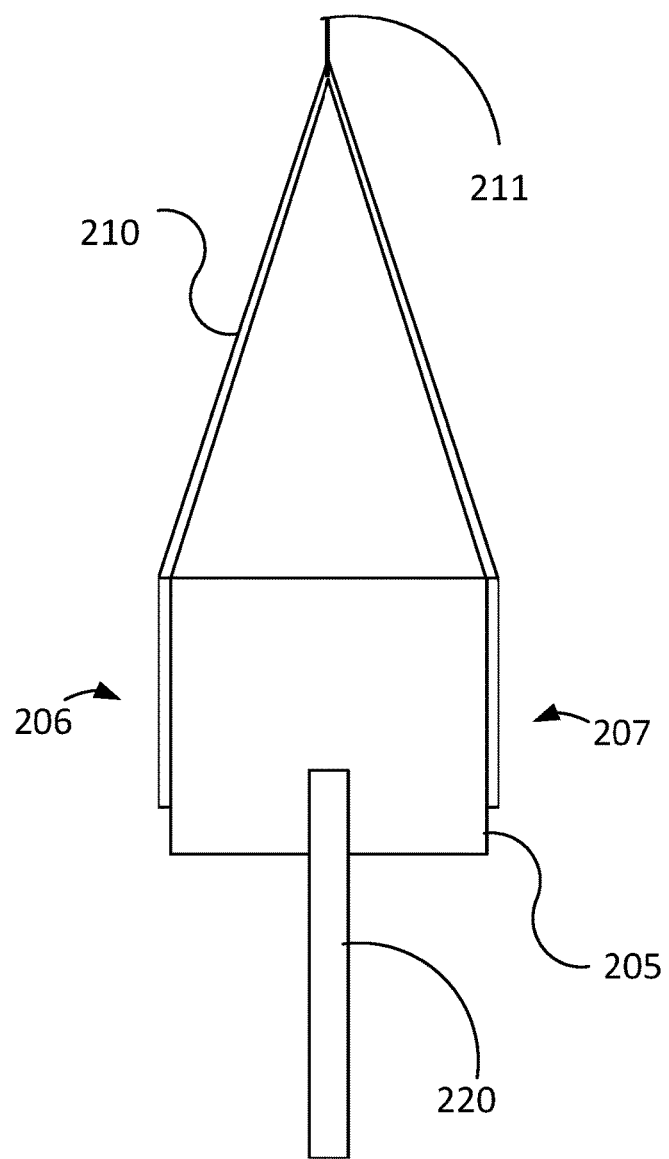
FIG. 6 is a side view of the suspension harness of the example embodiment shown in FIG. 5.

In a second aspect of the invention, a traction system is provided (shown in part in FIG. 1A). The system includes a traction device according to the any one of the embodiments of the first aspect of the invention. The system may further include a suspension harness 200 that includes a torso-engaging portion 205 configured to be disposed about on or more of the torso, hips and/or ribs of a patient. The suspension harness 200 also includes a first strap 210 and a second strap 215 each attached at one end to a front 206 of the torso-engaging portion 205 and at another end to a back 207 of the torso-engaging portion 205. A lower-appendage support strap 220 is also coupled to the torso-engaging portion 205. The top of each strap is coupled to a D-ring, O-Ring or other receptacle for coupling to the traction device 211. In operation, the first and second straps 210, 215 of the suspension harness 200 are removably coupled to a first and a second attachment ring 126, 135 or receptacle 127, 136 of either the top support 110 or the balance bar 125. As described below with respect to the third aspect of the invention, different types of traction may be achieved by coupling the harness 200 to either the top support 110 or balance bar 125. In one embodiment, chains or other linked cables 190 may be used to connect the first and second straps to the top support 110 or balance bar 125 via a removable connector 195, like a carabineer or a hook, in order to increase range of movement during traction-based exercises and to account for different patient heights, for example. FIG. 1A shows a pair of chains 190 each having a plurality of links extending between a first end and a second end, the pair of chains 190 each removably coupled to one of the at least two attachment rings 126, 135 or the at least two receptacles 127, 136 of the top support 110 via at least one of the plurality of links at the first end. The pair of chains 190 are each removably coupled to the balance bar 125 via at least one of the plurality of links that is arranged between the first end and second end of the pair of chains 190 and the pair of chains 190 are each configured to be coupled at the second end to one of a first strap 210 and a second strap 215 of a harness 200.

Figure 7:
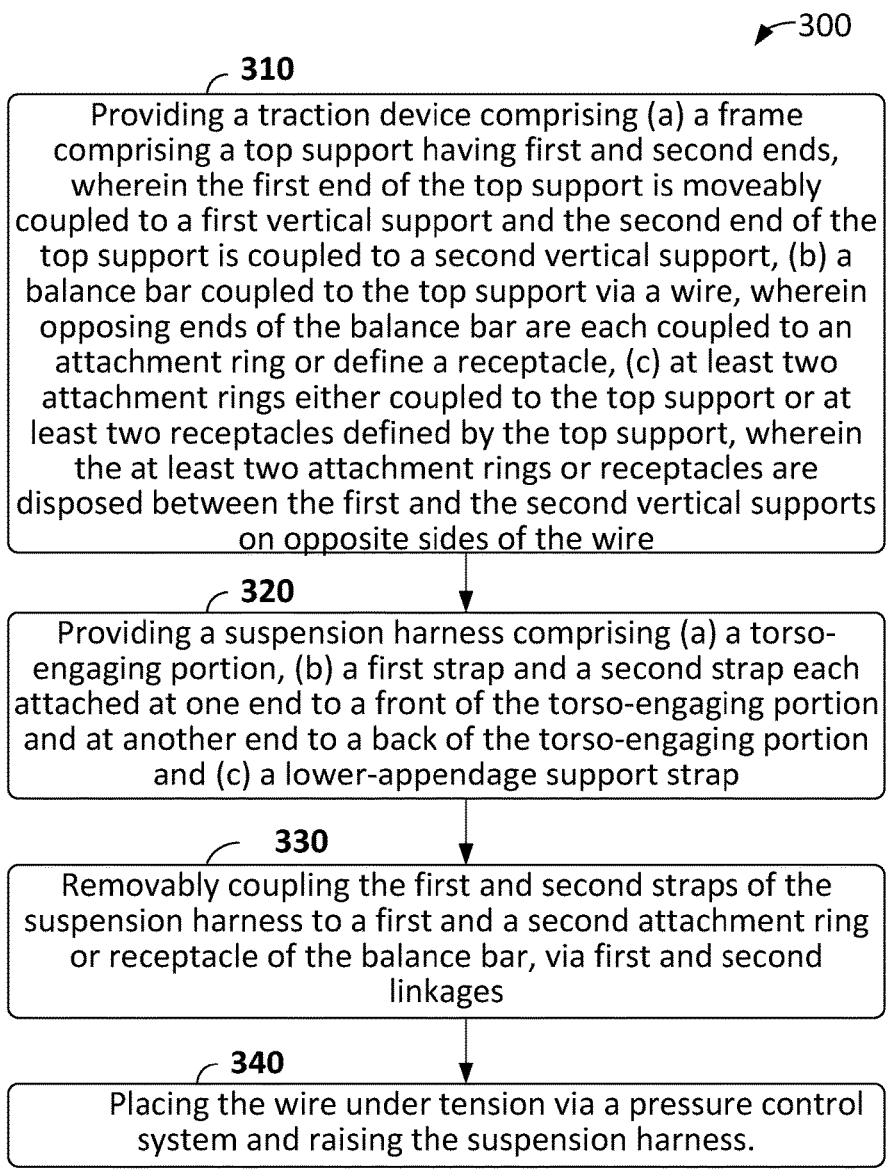
FIG. 7 is a flow chart of a method, according to an example embodiment.

In a third aspect of the invention, a method to induce traction is shown in FIG. 7. As shown by block 310, method 300 involves providing a traction device comprising (a) a frame comprising a top support having first and second ends, wherein the first end of the top support is moveably coupled to a first vertical support and the second end of the top support is coupled to a second vertical support, (b) a balance bar coupled to the top support via a wire, wherein opposing ends of the balance bar are each coupled to an attachment ring or define a receptacle, (c) at least two attachment rings either coupled to the top support or at least two receptacles defined by the top support, wherein the at least two attachment rings or receptacles are disposed between the first and the second vertical supports on opposite sides of the wire. Then at block 320, method 300 involves providing a suspension harness comprising (a) a torso-engaging portion, (b) a first strap and a second strap each attached at one end to a front of the torso-engaging portion and at another end to a back of the torso-engaging portion and (c) a lower-appendage support strap. Next, as shown in block 330, the method 300 includes the first and second straps of the suspension harness being removably coupled to a first and a second attachment ring or receptacle of the balance bar, via first and second linkages. Then, at block 340, the wire is placed under tension via a pressure control system and the suspension harness is raised towards the top support.

In this arrangement, nomadic decompression may be achieved and the amount of traction, flection and/or distraction may be advantageously controlled. For example, the first and second straps on the suspension harness may permit extenuation and/or diminishment of the lumbar curvature of a patient through gravitational pull, while a patient is in suspension. The balance bar 125 and wire 130 configuration may also permit a patient to lean and stretch side-to-side relieving pressure both sides of a respective disc. Traction may be achieved in this arrangement with a patient in upright standing traction, in a seated position on a seat member with feet raised off the ground or free hanging from the suspension with feet up and back.

In one embodiment, the method 300 may further include releasing the first and the second linkages from the first and the second attachment rings or receptacles of the balance bar. Then, the first and second straps of the suspension harness may be removably coupled to a first and a second attachment ring or receptacle of the top support, via third and fourth linkages. Alternatively, the first and second linkages may be used to connect the straps to the top support.

In this arrangement, the patient is suspended directly from the frame via first and second attachment rings and the first and second straps of the suspension harness. In this embodiment, traction is induced through the action of gravity. This may result in a deep-seated stretch with the body fully relaxed. In one embodiment, the legs may be disposed at a 90 degree angle. This arrangement has the unique benefit of being able to provide both flection and distraction of the spine.

In another embodiment, method 300 may further include vibrating the frame. In operation, vibration of the frame may translate to the suspension harness and may advantageously increase a patient's blood flow.

In an additional embodiment, method 300 may also include providing a seat member coupled to the frame or disposed on a base coupled to the frame and then moving the seat member relative to the frame. In this arrangement, the patient is in a seated position on the seat member with their knees at a 90 degree angle with their feet on a foot platform. In one embodiment, the patient maintains his knees in this position for 10-20 seconds and then straightens his knees for 3-5 seconds. In a preferred embodiment, the patient maintains his knees at a 90 degree angle for 10 seconds and then straightens his knees for 3 seconds. The knees are bent and straightened in this fashion for 5 to 15 minutes. When a patient first begins traction treatment, the patient may typically repeat the bending-straightening exercise for 5 minutes and may gradually build up to 15 minutes over time and additional treatments.

The above detailed description describes various features and functions of the disclosed traction device and methods for use thereof with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A traction device, comprising:
a frame comprising a top support having first and second ends, wherein the first end of the top support is coupled to a first vertical support and the second end of the top support is coupled to a second vertical support;
a balance bar moveably coupled to the top support via a wire such that the balance bar may be raised and lowered relative to the top support, wherein opposing ends of the balance bar are each coupled to an attachment ring or define a receptacle;
at least two attachment rings coupled to the top support or at least two receptacles defined by the top support, wherein the at least two attachment rings or the at least two receptacles are disposed between the first and the second vertical supports on opposite sides of a portion of the wire extending from the top support to the balance bar;

a pair of chains each having a plurality of links extending between a first end and a second end, the pair of chains each removably coupled to one of the at least two attachment rings or the at least two receptacles of the top support via at least one of the plurality of links at the first end, the pair of chains each removably coupled to the balance bar via at least one of the plurality of links that is arranged between the first end and second end of the pair of chains and the pair of chains each configured to be coupled at the second end to one of a first strap and a second strap of a harness; and a vibration apparatus coupled to the frame.

2. The traction device of claim 1, further comprising:
a base coupled to an end of the first vertical support and to an end of the second vertical support that are arranged opposite to the top support.

3. The traction device of claim 2, further comprising:
a foot platform coupled to one or more of the frame or the base.

4. The traction device of claim 3, wherein a plurality of hand rails extend between the first vertical support and the second vertical support above the foot platform.

5. The traction device of claim 2, further comprising:
a seat member movably coupled to the frame or in mechanical communication with a top surface of the base.

6. The traction device of claim 1, further comprising:
a plurality of attachment rings coupled to the balance bar or a plurality of receptacles defined by the balance bar; wherein the plurality of attachment rings or the plurality of receptacles are arranged along a length of the balance bar.

7. The traction device of claim 1, further comprising:
a housing coupled to the top support, wherein the housing defines a conduit;
a piston arranged within a cylinder and disposed in the conduit; and
a pressure control system configured to move the piston within the cylinder, wherein the wire has a first end and a second end, wherein the first end of the wire is coupled to the piston and the second end of the wire is coupled to a center of the balance bar.

8. The traction device of claim 7, further comprising:
a first rotatable support disposed in the housing adjacent to a location at which the wire extends from the housing or the top support, wherein the first rotatable support is in mechanical communication with the wire.

9. The traction device of claim 8, wherein the housing comprises a vertical section and a horizontal section, wherein the vertical section is disposed adjacent either the first or the second vertical support and the horizontal section is disposed adjacent to the top support of the frame.

10. The traction device of claim 9, further comprising:
a second rotatable support disposed in the housing between the piston and the first rotatable support at a junction of the vertical section and the horizontal section of the housing, wherein the second rotatable support is in mechanical communication with the wire.

11. The traction device of claim 1, further comprising:
a first plurality of attachment rings coupled to the top support or a first plurality of receptacles defined in the top support, wherein the first plurality of attachment rings or receptacles extend between the first vertical support and the portion of the wire extending from the top support to the balance bar; and
a second plurality of attachment rings coupled to the top support or a second plurality of receptacles defined in the top support, wherein the second plurality of attachment rings or receptacles extend between the second vertical support and the portion of the wire extending from the top support to the balance bar.

12. The traction device of claim 1, wherein the top support comprises a plurality of hand rails or grips having a spaced-apart arrangement.

13. The traction device of claim 1, wherein the first and second vertical supports each comprise a plurality of hand rails or grips having a vertically-extending, spaced-apart arrangement.

14. A traction system, comprising:
a traction device comprising (a) a frame comprising a top support having first and second ends, wherein the first end of the top support is coupled to a first vertical support and the second end of the top support is coupled to a second vertical support, (b) a balance bar moveably coupled to the top support via a wire such that the balance bar may be raised and lowered relative to the top support, wherein opposing ends of the balance bar are each coupled to an attachment ring or define a receptacle, (c) at least two attachment rings coupled to the top support or at least two receptacles defined by the top support, wherein the at least two attachment rings or receptacles are disposed between the first and the second vertical supports on opposite sides of a portion of the wire extending from the top support to the balance bar;

a suspension harness comprising (a) a torso-engaging portion, (b) a first strap and a second strap each attached at one end to a front of the torso-engaging portion and at another end to a back of the torso-engaging portion and (c) a lower-appendage support strap; and a pair of chains each having a plurality of links extending between a first end and a second end, the pair of chains each removably coupled to one of the at least two attachment rings or the at least two receptacles of the top support via at least one of the plurality of links at the first end, the pair of chains each removably coupled to the balance bar via at least one of the plurality of links that is arranged between the first end and second end of the pair of chains and the pair of chains each removably coupled at the second end to one of the first strap and the second strap of the harness, wherein the pair of chains are configured to increase range of movement during traction-based exercises or to account for different patient heights.

* * * * *